US008039444B2

(12) United States Patent
Raoof et al.

(10) Patent No.: US 8,039,444 B2
(45) Date of Patent: *Oct. 18, 2011

(54) ANTISENSE PERMEATION ENHANCERS

(75) Inventors: Araz A. Raoof, Dublin (IE); Mangaraju Gudipati, Yardley, PA (US); David C. Bibby, Emeryville, CA (US); Susan Weinbach, San Diego, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/509,529

(22) Filed: Aug. 23, 2006

(65) Prior Publication Data

US 2007/0004668 A1  Jan. 4, 2007

Related U.S. Application Data

(63) Continuation of application No. 10/145,181, filed on May 13, 2002, now abandoned.

(60) Provisional application No. 60/290,436, filed on May 11, 2001.

(51) Int. Cl.
*A61K 48/00* (2006.01)
*A61K 31/20* (2006.01)

(52) U.S. Cl. .................. 514/44 A; 514/558; 536/25

(58) Field of Classification Search .................. 514/44, 514/558; 536/25
See application file for complete search history.

(56) References Cited

U.S. PATENT DOCUMENTS

| | | | |
|---|---|---|---|
| 4,469,671 A | 9/1984 | Zimmerman et al. | |
| 4,525,339 A | 6/1985 | Behl et al. | |
| 4,645,502 A | 2/1987 | Gale et al. | |
| 4,656,161 A | 4/1987 | Herr | |
| 4,692,452 A | 9/1987 | Cerny et al. | |
| 4,789,547 A | 12/1988 | Song et al. | |
| 4,906,463 A | 3/1990 | Cleary et al. | |
| 4,910,205 A | 3/1990 | Kogan et al. | |
| 4,911,916 A | 3/1990 | Cleary | |
| 4,994,273 A | 2/1991 | Zentner et al. | |
| 5,087,620 A | 2/1992 | Parab | |
| 5,091,171 A | 2/1992 | Yu et al. | |
| 5,190,748 A | 3/1993 | Bachynsky et al. | |
| 5,229,130 A | 7/1993 | Sharma et al. | |
| 5,288,497 A | 2/1994 | Stanley et al. | |
| 5,374,633 A | 12/1994 | Parab | |
| 5,399,355 A | 3/1995 | Riedl et al. | |
| 5,492,698 A | 2/1996 | Von Kleinsorgen | |
| 5,541,155 A | 7/1996 | Leone-Bay et al. | |
| 5,580,574 A | 12/1996 | Behl et al. | |
| 5,650,386 A | 7/1997 | Leone-Bay et al. | |
| 5,662,926 A | 9/1997 | Wick et al. | |
| 5,714,477 A | 2/1998 | Einarsson | |
| 5,801,154 A | 9/1998 | Baracchini et al. | |
| 5,834,010 A | 11/1998 | Quan et al. | |
| 5,837,289 A | 11/1998 | Grasela et al. | |
| 5,854,281 A | 12/1998 | Uekama et al. | |
| 5,863,555 A | 1/1999 | Heiber et al. | |
| 5,866,157 A | 2/1999 | Higo et al. | |
| 5,912,009 A | 6/1999 | Venkateshwaran et al. | |
| 5,952,000 A | 9/1999 | Venkateshwaran et al. | |
| 5,977,175 A | 11/1999 | Lin | |
| 6,001,390 A | 12/1999 | Yum et al. | |
| 6,010,716 A | 1/2000 | Saunal et al. | |
| 6,051,609 A | 4/2000 | Yu et al. | |
| 6,132,760 A | 10/2000 | Hedenstrom et al. | |
| 6,153,209 A | 11/2000 | Vega et al. | |
| 6,200,602 B1 | 3/2001 | Watts et al. | |
| 6,203,817 B1 | 3/2001 | Cormier et al. | |
| 6,262,161 B1 | 7/2001 | Kawaji et al. | |
| 6,264,981 B1 | 7/2001 | Zhang et al. | |
| 6,267,985 B1 | 7/2001 | Chen et al. | |
| 6,268,355 B1 | 7/2001 | Mizobuchi et al. | |
| 6,326,360 B1 | 12/2001 | Kanazawa et al. | |
| 6,379,960 B1 | 4/2002 | Popoff | |
| 6,582,908 B2 | 6/2003 | Fodor et al. | |
| 2001/0053519 A1 | 12/2001 | Fodor et al. | |
| 2003/0018085 A1 | 1/2003 | Raoof et al. | |
| 2003/0228597 A1 | 12/2003 | Cowsert et al. | |
| 2007/0031844 A1 | 2/2007 | Khvorova et al. | |

FOREIGN PATENT DOCUMENTS

| | | |
|---|---|---|
| EP | 0 370 481 | 5/1990 |
| EP | 0 376 534 | 7/1990 |
| EP | 0 497 162 | 8/1992 |
| EP | 0 517 211 | 12/1992 |
| EP | 0 580 074 | 1/1994 |
| GB | 953 626 | 3/1964 |
| JP | 51 031687 | 3/1976 |
| JP | 2-207018 | 8/1990 |
| JP | 02-207018 | 8/1990 |
| JP | 2-282327 | 11/1990 |
| JP | 6-40949 | 2/1994 |
| JP | 11-35458 | 2/1999 |
| WO | WO 84/04674 | 12/1984 |
| WO | WO 93/21907 | 11/1993 |

(Continued)

OTHER PUBLICATIONS

Muranishi, Critical Reviews in Therapeutic Drug Carrier Systems, 1990, 7(1), 1-33.*
Branch et al., "A good antisense molecule is hard to find," TIBS (1998) 23:45-50.
Chin, Andrew "On the Preparation and Utilization of Isolated and Purified Oligonucleotides." Document purportedly located on a CD-ROM and contributed to the public collection of the Katherine R. Everett Law Library of the University of North Carolina on Mar. 14, 2002.

(Continued)

*Primary Examiner* — Shaojia Anna Jiang
*Assistant Examiner* — Ganapathy Krishnan
(74) *Attorney, Agent, or Firm* — Knobbe Martens Olsen & Bear

(57) ABSTRACT

A pharmaceutical composition comprising an antisense oligonucleotide and a permeation enhancer that comprises a multi-carbon backbone having a functional group and also one or more side chains which have one or more carbon atoms and, optionally, one or more functional groups.

20 Claims, No Drawings

FOREIGN PATENT DOCUMENTS

| WO | WO 95/22319 | | 8/1995 |
|---|---|---|---|
| WO | WO 95/34294 | | 12/1995 |
| WO | WO 97/05903 | | 2/1997 |
| WO | WO 99/01579 | | 1/1999 |
| WO | WO 99/02120 | * | 1/1999 |
| WO | WO 99/02485 | | 1/1999 |
| WO | WO 99/45934 | | 9/1999 |
| WO | WO 99/60012 | * | 11/1999 |
| WO | WO 00/22909 | | 4/2000 |
| WO | WO 00/50012 | | 8/2000 |
| WO | WO 02/092070 | | 11/2002 |

OTHER PUBLICATIONS

Crooke et al., "Basic Principles of Antisense Therapeutics" Antisense Research and Application (1998) Chapter 1:1-50.

Cumming et al., "In vitro evaluation of a series of sodium carboxylates as dermal penetration enhancers" International Journal of Pharmaceuticals (1994) 108(2):141-148.

International Search Report from PCT/US2002/015166, dated Sep. 19, 2002.

New England BioLabs, Inc. Catalogue (1998): 121, 284.

Reynolds et al., Rational siRNA design for RNA interference, Mar. 2004, Nature Biotechnology, vol. 22, pp. 326-330.

Sanghvi et al., "Heterocyclic Base Modifications in Nucleic Acids and Their Applications in Antisense Oligonucleotides" Antisense Research and Applications (1993) pp. 273-288.

Supplementary European Search Report for Application EP 02731781 dated Jun. 6, 2008.

Anderberg et al., "Sodium Caprate Elicits Dilatations in Human Intestinal Tight Junctions and Enhances Drug Absorption by the Paracellular Route", Pharmaceutical Research (1993), 10:857-864.

Artursson, P., "Epithelial Transport of Drugs in Cell Culture. I: A model for Studying the Passive Diffusion of Drugs over Intestinal Absorbative (Caco-2) Cells", J. Pharmaceutical Studies (1990), 79: 476-482.

Aungst, "Structure/Effect Studies of Fatty Acid Isomers as Skin Penetration Enhancers and Skin Irritants" Phamaceutical Research 6(3):244-247 (1989).

Aungst, et al., "Enhancement of the Intestinal Absorption of Peptides and Non-peptides", J. of Controlled Release (1996), 41:19-31.

Bennett et al, "Pulmonary Delivery of Detirelix Intratracheal Instillation and Aerosol Inhalation in the Briefly Anesthetized Dog", Pharmaceutical Research (1994), vol. 11, No. 7, 1048-1054.

Brayden et al, "Heparin Absorption Across the Intestine: Effects of Sodium N-[8-(2-Hydroxybenzoyl)Amino]Caprylate in Rat in Situ Intestinal Instillations and in Caco-2 Monolayers", Pharmaceutical Research, 1997, 14(12), 1772-1779.

Doluisio et al, "Drug Absorption I: An in Situ Rat Gut Technique Yielding Realistic Absorption Rates", J. Pharmaceutical Studies (1969), 59:1196-1200.

Gennaro, A.R., Remingtion: The Science and Practice of Pharmacy (1995), 1618.

Lee et al, "Critical Reviews in Therapeutic Drug Carrier Systems", 1991, 8(2), 91-192.

Lindmark et al., "Mechanism of Absorption Enhancement in Humans After Rectal Administration of Ampicillin in Suppositories Containing Sodium Caprate", Pharmaceutical Research (1997), 14:930-935.

Oda et al, Proc. Int'l Symp. Control. Rel. Bioact. Mater. 24 (1997) 283-284.

Schneider et al. "Evaluation of Drug Penetration into Human Skin Ex Vivo Using Branched Fatty Acids and Propylene Glycol" International Journal of Pharmaceutics 145:187-196 (1996).

Tomita et al., "Enhancement of Colonic Drug Absorption by the Paracellular Permeation Route", Pharmaceutical Research (1988), 5:341-346.

Yeh et al,Effect of Medium-chain Glycerides on Physiological Properties of Rabbit Intestinal Epithelium in Vitro, Pharmaceutical Research (1994), 11:1148-1154.

English translation of abstract of Japanese Patent Application No. JP 03 275 633, filed Dec. 6, 1991.

English translation of abstract of Japanese Patent Application No. JP 2004529953, filed Sep. 30, 2004.

English translation of abstract of Japanese Patent Application No. JP 59 073 600, filed Apr. 25, 1984.

English translation of abstract of Russian Patent Application No. RU 2 068 689, filed Nov. 10, 1996.

* cited by examiner

ANTISENSE PERMEATION ENHANCERS

CROSS REFERENCE TO RELATED APPLICATIONS

This application is a continuation of U.S. application Ser. No. 10/145,181, filed May 13, 2002, which is hereby incorporated by reference, which is based on and claims priority to U.S. Provisional Application No. 60/290,436, filed May 11, 2001.

PARTIES OF JOINT RESEARCH AGREEMENT

The present invention was made as a result of activities undertaken within the scope of a written joint research agreement between Elan Corporation, PLC, Elan International Services, Ltd., Isis Pharmaceuticals, Inc., and Orasense Ltd.

FIELD OF THE INVENTION

The present invention relates to permeation enhancers that are useful in the administration of a drug.

Drug delivery systems generally involve a permeation step followed by absorption into the circulatory system. For example, a drug can be applied through the skin by use of a transdermal patch which comprises a drug and a film or fabric and which is adhered to the outer skin of the patient. Drugs may also be delivered across a mucous membrane or other cellular membrane (collectively "transmucosal"), for example, by: (A) aerosol delivery of the drug to the nose or lungs; (B) oral ingestion of the drug followed by permeation through the gastrointestinal wall; and (C) the dissolution of lozenges or pills held between the cheek and gum or under the tongue followed by transport through the membranes of the mouth.

During the early development of transdermal delivery systems, investigators found that the oily, hydrophobic nature of the skin reduces significantly the absorption rate of aqueous drug solutions or dispersions. Thus, the natural barrier properties of skin, which protect the body against the ingress of foreign substances, act also as barriers to applied drugs, thereby reducing their rate of permeation and ultimately their bioavailability. Problems are encountered also in delivering drugs in a satisfactory way by transmucosal means. The rate of drug permeation is an important factor in achieving bioavailability and pharmaceutically useful concentrations of the drug at the target membrane. It is not surprising that considerable effort has been dedicated toward the objective of enhancing the rate of drug permeation through the skin or by transmucosal means. Examples of such efforts are summarized below.

REPORTED DEVELOPMENTS

U.S. Pat. No. 5,854,281 (Uekama, et al.) teaches the use of straight chain fatty acids, salts, and esters thereof to enhance the percutaneous permeability of prostaglandin. U.S. Pat. Nos. 5,952,000 and 5,912,009 (Venkateshwaran, et al.) disclose drug delivery systems that are enhanced by the presence of a fatty acid ester of lactic acid (or salts thereof) and a fatty acid ester (or salts thereof) of glycolic acid respectively. The use of glycerides of fatty acids to enhance the skin permeation of a biologically active pergolide is disclosed in U.S. Pat. No. 6,001,390 (Yum, et al.). U.S. Pat. No. 4,789,547 teaches the enhancement of drug permeation through the skin by a saturated or unsaturated fatty acid in a solvent such as propylene glycol. Published PCT application WO00/22909 discloses oral delivery systems for pharmaceutical or other biologically active substances wherein the pharmaceutical or other substance is coated or complexed with a carboxylic acid to enable the substance to transit the stomach and to be absorbed in the intestine. The coating or complexing is achieved by means of co-precipitation from an acidic solution of the active substance and carboxylic acid, which is described as having from nine to 30 carbon atoms in a straight or branched chain, saturated or unsaturated, acyclic or cyclic structure and further substituted or unsubstituted with functional groups such as steroid rings, phenyl groups and the like. WO00/22909 discloses specific examples of complexes formed from the straight chain, saturated or unsaturated or steroidal carboxylic acids, dodecanoic acid, tetradecanoic acid, hexadecanoic acid, octadecanoic acid, oleic acid. palmitoleic acid, ricinoleic acid and fusidic acid.

Investigators continue to seek ways to safely and effectively administer pharmaceutical agents by transmucosal or transdermal routes. Obstacles to these goals are the complexity and variability in the properties of the various types of membranes and the skin. Furthermore, for large molecule pharmaceutical agents, for example, antisense oligonucleotides, passage through these various membranes and the skin is particularly difficult. In light of the recognized need to overcome the natural barrier properties of bodily membranes and skin in achieving bioavailability of antisense oligonucleotides, the present invention relates to the provision of a class of compounds that enhance the permeation of antisense oligonucleotides for delivery to a patient.

SUMMARY OF THE INVENTION

In accordance with the present invention, there is provided a composition comprising an antisense compound and a compound which is effective in enhancing the bioavailability of said antisense compound and which comprises a multi-carbon backbone having a functional group and also one or more side chains which have one or more carbon atoms and, optionally, one or more functional groups. A preferred class of bioavailability-enhancing compounds comprises a compound of Formula I below.

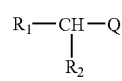

Formula I wherein, Q is
  (1) a partially or completely neutralized —COOH, or
  (2) a partially or completely neutralized —SO$_3$H, or
  (3) a mono- or di-substituted alkyl or alkenyl group having one to about twelve carbon atoms, the substituent(s) thereof being a partially or completely neutralized —COOH or partially or completely neutralized —SO$_3$H;

R$_1$ and R$_2$ are independently
  (1) an unsubstituted alkyl or alkenyl group having one to about twelve carbon atoms, or
  (2) a substituted alkyl or alkenyl group having one to about twelve carbon atoms, the substituent thereof being selected from the group consisting of
    (i) partially or completely neutralized —COOH,
    (ii) partially or completely neutralized —SO$_3$H,
    (iii) —NH$_2$,
    (iv) —CONH$_2$; and
    (v) —OH.

In preferred form, the antisense compound comprises an antisense oligonucleotide. Preferably, the antisense oligonucleotide comprises a modification selected from the group consisting of base modifications, internucleotide linkage modifications and sugar moiety modifications. In a preferred form, the antisense oligonucleotide has a modified sugar moiety wherein the modification is a 2'-O-(2-methoxyethyl) modification. Also, in preferred form, the enhancer comprises a compound in which Q is partially or completely neutralized —COOH.

Another aspect of the present invention includes a method of treating a condition in a patient comprising administering to the patient a composition which comprises an antisense oligonucleotide in a pharmaceutically effective amount and a permeation enhancer of Formula I above in an enhancing-effective amount.

As explained below, a particular advantage of the present invention is that it provides to the medical and pharmaceutical professions a compound that enhances the permeation of an antisense oligonucleotide into and through the intestinal barrier of a subject.

DETAILED DESCRIPTION OF THE INVENTION

As mentioned above, the composition of the present invention comprises an antisense compound, a compound that is characterized herein as a permeation enhancer, and, optionally, a vehicle. In selecting a permeation enhancer from among the compounds represented by Formula I, consideration is given to both the nature of the antisense compound employed and to the tendency of the target membrane or skin to absorb the antisense compound. As will become evident from the following discussion, there is included within the class of enhancer compounds of the present invention compounds that have a wide range of hydrophobic-hydrophilic properties and that may be described as branched chain compounds.

The compounds of Formula I comprise a multi-carbon backbone having a functional group and also a side chain(s) which has one or more carbon atoms and, optionally, one or more functional groups. The compounds are therefore distinguished from the straight chain carboxylic acids reported in the literature as having permeation enhancer properties. Each of $R_1$ and $R_2$ of Formula I represents an unsubstituted alkyl or unsubstituted alkenyl group having 1 to about 12 carbon atoms or a substituted alkyl or substituted alkenyl group having 1 to about 12 carbon atoms, or one of $R_1$ or $R_2$ can be a substituted alkyl or substituted alkenyl group having 1 to about 12 carbon atoms and the other an unsubstituted alkyl or unsubstituted alkenyl group. Each of $R_1$ and $R_2$ of Formula I may be a straight chain, branched, or cyclo-aliphatic group.

In addition, one of $R_1$ or $R_2$ can be an alkyl group and the other an alkenyl group. Examples of alkyl groups are methyl, ethyl, isopropyl, hexyl, octyl, decyl, and dodecyl. Preferably, the alkyl group has at least about 4 to about 12 carbon atoms. Examples of alkenyl groups are octenyl, pentenyl, and dodecenyl. Preferably, the alkenyl group has at least about 4 to about 12 carbon atoms.

Also, in preferred form, the sum of the carbon atoms in $R_1$ and $R_2$ is at least about 16. In a particularly preferred form of the invention, $R_1$ is alkyl and $R_2$ is alkyl. For those enhancers in which $R_1$ and/or $R_2$ includes a substituted alkyl or substituted alkenyl group, it is preferred that the substituent thereof is a hydroxyl group.

As set forth in Formula I, enhancer compounds useful in the present invention can include a partially or completely neutralized —COOH or —SO$_3$H group. As used herein, the term "neutralized" means the reaction product of the carboxylic acid or sulfonic acid with a base that is present in an amount sufficient to react with all of the acid. As used herein, the term "partially neutralized" means the reaction product of the carboxylic or sulfonic acid with an amount of base that reacts with less than all of the acid, but with at least about 50% of the acid. Examples of bases that can be used are sodium hydroxide, sodium carbonate, potassium hydroxide, magnesium hydroxide, calcium hydroxide, ammonium hydroxide, and trialkyl amine. Preferably, -Q of Formula I is the sodium salt of —COOH. For those enhancers where -Q of Formula I is a substituted alkyl or substituted alkenyl group, the following are examples of such groups: methyl, hexyl, octyl, and dodecyl. Preferably, the total number of carbon atoms in the alkyl or alkenyl group is about one to about 12, with an alkyl group being preferred.

In a preferred group of compounds of Formula I, $R_1$ is $C_6$-$C_{12}$ alkyl, $R_2$ is $C_4$-$C_{10}$ alkyl, and -Q is neutralized —COOH. Particularly preferred permeation enhancers are compounds represented by Formula I wherein $R_1$ is $C_{6-8}$ alkyl, $R_{2is}$ is $C_{8-10}$ alkyl, and -Q is —COONa.

A preferred enhancer compound useful in the present invention comprises the sodium salt of a carboxylic acid of Formula I in which $R_1$ is an alkyl group having ten carbon atoms ($C_{10}H_{21}$) and $R_2$ is an alkyl group having eight carbon atoms ($C_8H_{17}$) sodium 2-n-octyl-dodecanoate. Other preferred enhancer compounds include sodium 2-n-hexyl-decanoate and sodium 2-n-butyl-octanoate.

The enhancer compounds useful in the present invention can include a chiral center. When the enhancer compound includes a chiral center, it may be used as a racemic mixture of optical isomers, or optionally as the essentially pure D or L isomers of the enhancer compound.

Enhancer compounds within the scope of the present invention are known. It will be recognized that preparation of the enhancer compounds is well within the purview of one of ordinary skill in the art. Speaking generally, the enhancer carboxylic acids useful in the present invention can be prepared according to known preparative methods. Non-limiting examples of preparative methods include the oxidative cleavage of an appropriately unsaturated hydrocarbon with a strong oxidizing agent and the saponification of a corresponding ester. A non-limiting example of a typical ester is the glyceride of the desired acid.

Neutralization of a carboxylic acid or sulfonic acid with an alkali such as sodium hydroxide is generally carried out by adding the alkali to a stirred solution of the acid dissolved in water or a mixture of water and alcohol.

The enhancer of Formula I can be mono-functional or multi-functional. The degree of functionality and length of the carbon chain are related to the hydrophilic-hydrophobic (lipophilic) nature of the enhancer compounds. In general, the higher the degree of functionality, the more hydrophilic is the compound. Also, speaking to generally, the greater the number of carbon atoms in the compound, the more hydrophobic the compound is. Improved delivery of antisense oligonucleotides can be achieved when the hydrophobic-hydrophilic balance of the enhancer is matched appropriately to the drug and to the targeted tissue. Selecting -$R_1$, -$R_2$ and -Q with relatively long carbon chains can provide enhancers having a relatively high degree of hydrophobicity. In contrast, enhancers with relatively short carbon chains and with multi-functional groups have a relatively high degree of hydrophilicity.

The composition of the present invention may comprise an enhancer compound of Formula I in admixture with one or more other enhancers, for example, a straight chain fatty acid, an ester or salt thereof, or compounds that promote the formation of liposomes, or a micro emulsion. When additional enhancer compounds are used, they may be present in a weight ratio of up to about 99 parts of the additional enhancer for each part of a salt of Formula 1. The range of mixtures of an additional enhancer:salt of Formula 1 by weight ratio which are preferred are from about 99:1 to about 1:99.

In preferred form, a composition comprising an enhancer compound of the present invention (those of Formula I) and additional other enhancer compounds, the enhancer compounds of Formula I comprise no more than by weight about 50% of the enhancer compounds present.

When enhancer compounds of the present invention are mixed with other enhancer compounds in formulations used in connection with delivery of a drug comprising an antisense nucleotide, typically the enhancer compounds of Formula I comprises, by weight, at least about 10% of the enhancer compounds present in the formulations.

The compositions of the present invention comprise also antisense compounds particularly antisense oligonucleotides used to treat disease states that result from undesirable levels of protein production and/or activity in the body. These antisense compounds specifically hybridize with one or more target nucleic acids encoding a protein involved in a given disease state.

As used herein, the term "target nucleic acid" encompasses DNA encoding a protein, RNA (including pre-mRNA and mRNA) transcribed from such DNA, and also cDNA derived from such RNA. The specific hybridization of an antisense compound with its target nucleic acid interferes with the normal function of the nucleic acid. This modulation of function of a target nucleic acid by compounds that specifically hybridize to it is generally referred to as "antisense". The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of the protein encoded by the nucleic acid. In the context of the present invention, "modulation" means either an increase (stimulation) or a decrease (inhibition) in the expression of a gene. In the context of the present invention, inhibition is the preferred form of modulation of gene expression and mRNA is a preferred target.

It is preferred to target specific nucleic acids with the antisense oligonucleotides of the present invention. "Targeting" an antisense compound to a particular nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding a protein, regardless of the sequence(s) of such codons.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

Once one or more target sites have been identified, oligonucleotides are chosen which are sufficiently complementary to the target, i.e., hybridize sufficiently well and with sufficient specificity, to give the desired effect.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense oligonucleotide need not be 100% complementary to that of its target nucleic acid to be specifically hybridizable. An antisense oligonucleotide is specifically hybridizable when binding of the compound to the target DNA or RNA molecule interferes with the normal function of the target DNA or RNA to cause a loss of utility, and there is a sufficient degree of complementarity to avoid non-specific binding of the antisense oligonucleotide to non-target sequences under conditions in which specific binding is desired, i.e., under physiological conditions in the case of in vivo assays or therapeutic treatment, and in the case of in vitro assays, under conditions in which the assays are performed.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 50 nucleobases (i.e. from about 8 to about 50 linked nucleosides). Particularly preferred antisense compounds are antisense oligonucleotides, even more preferably those comprising from about 12 to about 25 nucleobases. Even more preferably, the antisense oligonucleotides comprise from about 15 to about 20 nucleobases. In a most preferred embodiment, the antisense oligonucleotides of the present invention comprise about 20 nucleobases. Antisense compounds include ribozymes, external guide sequence (EGS) oligonucleotides (oligozymes), and other short catalytic RNAs or catalytic oligonucleotides which hybridize to the target nucleic acid and modulate its expression.

In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

Specific examples of preferred antisense compounds useful in this invention include oligonucleotides containing modified backbones or non-natural internucleoside linkages.

As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone.

Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

Most preferred embodiments of the invention are oligonucleotides with phosphorothioate backbones and oligonucleosides with heteroatom backbones, and in particular —CH$_2$—NH—O—CH$_2$—, —CH$_2$—N(CH$_3$)—O—CH$_2$— [known as a methylene(methylimino) or MMI backbone], —CH$_2$—O—N(CH$_3$)—CH$_2$—, —CH$_2$—N(CH$_3$)—N(CH$_3$)—CH$_2$— and —O—N(CH$_3$)—CH$_2$—CH$_2$— [wherein the native phosphodiester backbone is represented as —O—P—O—CH$_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C$_1$ to C$_{10}$ alkyl or C$_2$ to C$_{10}$ alkenyl and alkynyl. Particularly preferred are O[(CH$_2$)$_n$O]$_m$CH$_3$, O(CH$_2$)$_n$OCH$_3$, O(CH$_2$)$_n$NH$_2$, O(CH$_2$)$_n$CH$_3$, O(CH$_2$)$_n$ONH$_2$, and O(CH$_2$)$_n$ON[(CH$_2$)$_n$CH$_3$)]$_2$, where n and m are from 1 to about 10. Other preferred oligonucleotides comprise one of the following at the 2' position: C$_1$ to C$_{10}$ lower alkyl, substituted lower alkyl, alkenyl, alkynyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2-O—CH$_2$CH$_2$OCH$_3$, also known as 2'-O-(2-methoxyethyl) or 2'-MOE) (Martin et al., Helv. Chim. Acta, 1995, 78, 486-504) i.e., an alkoxyalkoxy group. A further preferred modification includes 2'-dimethylaminooxyethoxy, i.e., a O(CH$_2$)$_2$ON(CH$_3$)$_2$ group, also known as 2'-DMAOE, and 2'-dimethylaminoethoxyethoxy (also known in the art as 2'-dimethylaminoethoxyethyl or 2'-DMAEOE), i.e., 2'-O—CH$_2$—O—CH$_2$—N(CH$_3$)$_2$.

A further preferred modification includes Locked Nucleic Acids (LNAs) in which the 2'-hydroxyl group is linked to the 3' or 4' carbon atom of the sugar ring thereby forming a bicyclic sugar moiety. The linkage is preferably a methelyne (—CH$_2$—)$_n$ group bridging the 2' oxygen atom and the 4' carbon atom wherein n is 1 or 2. LNAs and preparation thereof are described in WO 98/39352 and WO 99/14226.

Other preferred modifications include 2'-methoxy (2'-O—CH$_3$), 2'-aminopropoxy (2'-OCH$_2$CH$_2$CH$_2$NH$_2$), 2'-allyl (2'-CH$_2$—CH=CH$_2$), 2'-O-allyl (2'-O—CH$_2$—CH=CH$_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, each of which is herein incorporated by reference in its entirety.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine (1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B. ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2.degree. C. (Sanghvi, Y. S., Crooke, S. T. and Lebleu, B., eds., Antisense Research and Applications, CRC Press, Boca Raton, 1993, pp. 276-278) and are presently preferred base substitutions, even more particularly when combined with 2'-O-(2-methoxyethyl) sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; 5,681,941, and 5,750,692, each of which is herein incorporated by reference.

Another modification of the oligonucleotides of the invention involves chemically linking to the oligonucleotide one or more moieties or conjugates which enhance the activity, cellular distribution or cellular uptake of the oligonucleotide. The compounds of the invention can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992 the entire disclosure of which is incorporated herein by reference. Conjugate moieties include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenarnic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference in its entirety.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The antisense compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993 or in WO 94/26764 and U.S. Pat. No. 5,770,713 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

The antisense compounds of the present invention can be utilized for diagnostics, therapeutics, prophylaxis and as research reagents and kits. For therapeutic use, an animal, preferably a human, suspected of having a disease or disorder which can be treated by modulating the expression of a protein is treated by administering antisense oligonucleotides in accordance with this invention. The specificity and sensitivity of antisense is particularly useful in therapeutic applications and antisense oligonucleotides have been employed as therapeutic moieties in the treatment of disease states in animals and man. Antisense oligonucleotide drugs, including ribozymes, have been safely and effectively administered to humans and numerous clinical trials are presently underway. It is thus established that oligonucleotides can be useful therapeutic modalities that can be configured to be useful in treatment regimes for treatment of cells, tissues and animals, especially humans. The compounds of the invention can be utilized in pharmaceutical compositions by adding an effective amount of an antisense oligonucleotide to a suitable pharmaceutically acceptable diluent or carrier. Use of the antisense oligonucleotides and methods of the invention may also be useful prophylactically, e.g., to prevent or delay infection, inflammation or tumor formation, for example.

The antisense oligonucleotides of the invention are useful for research and diagnostics, because these compounds hybridize to nucleic acids encoding a protein involved in a disease state, enabling sandwich and other assays to easily be constructed to exploit this fact. Hybridization of the antisense oligonucleotides of the invention with a nucleic acid encoding a protein involved in a disease state can be detected by means known in the art. Such means may include conjugation of an enzyme to the oligonucleotide, radiolabelling of the oligonucleotide or any other suitable detection means. Kits using such detection means for detecting the level of a protein involved in a disease state in a sample may also be prepared.

It is believed that the present invention will be used most widely with antisense oligonucleotides whose bioavailability and/or absorption properties can be enhanced by use of the permeation enhancer of the present invention. It is believed also that the present invention can be used to a particularly good effect by combining the permeation enhancer of the present invention with an antisense oligonucleotide that is ingested orally and absorbed relatively poorly in the gastrointestinal tract ("GIT").

The antisense oligonucleotide can be in any suitable form, for example, in crystalline or amorphous form and in solid, liquid, or gel form, for example, in the form of nano particles and micro particles or in larger particle-size form. In addition, the antisense oligonucleotide can be present in the composition in a time-release form.

The composition of the present invention comprises a pharmaceutically effective amount of the antisense oligonucleotide, that is, an amount that is effective in achieving the desired prophylactic, therapeutic or diagnostic effect in the patient. It should be appreciated that the amount of antisense oligonucleotide comprising the composition will depend on various factors, including, for example, the particular antisense oligonucleotide used, the nature of the condition to be treated, and the nature of the patient.

Similarly, the enhancer compound contained in the composition of the present invention is present in an amount that is effective in increasing the bioavailability and/or absorption properties of the antisense oligonucleotide. The amount of enhancer in the composition will depend on various factors, including, for example, the presence of other enhancer compounds, the particular antisense oligonucleotide(s) used, the amount of antisense oligonucleotide(s) employed, the dosage form selected, the nature of the dosage form, the nature of the enhancer, the particular enhancer compound used, the optical purity of the enhancer compound used, that is whether it is used in the form of a pure isomer or as a partially or completely racemic mixture. It is believed that, for most applications, the composition will comprise an antisense oligonucleotide: enhancer ratio of about 1:99 to about 99:1. Typically, the ratio will be between about 1:20 and about 20:1. This ratio range is given for guideline purposes, with the understanding that ratios of antisense oligonucleotide to enhancer outside of this range may be used depending on the various factors mentioned above.

The composition of the present invention comprises optionally a vehicle, the nature of which will depend on the form of the composition. The composition can be used in any suitable form, for example, in the form of a granulate, solid, semi-solid, solution, suspension, tablet, capsule, inhalant, suppository, or enema. The tablets and capsules can be in the form, for example, of delayed release, sustained release, or immediate release systems. It is believed that the composition of the present invention will be used most widely in solid or semi-solid oral dosage form.

The term "vehicle" is used broadly to include various types of pharmaceutically acceptable ingredients that can comprise the composition other than the drug and enhancer constituents of the composition. Examples of vehicles include fillers, diluents, excipients and materials, which have an effect on the release properties of the antisense oligonucleotide or on the enhancer compound(s), that is, control-release materials. Examples of fillers and diluents include lactose, mannitol, dextrose, vegetable oils, glycerides, and microcrystalline cellulose. Examples of excipients include phosphate and citrate salts, magnesium stearate, silica, and binders such as hydroxypropyl methylcellulose, polyvinylpyrrolidone, and starch. Examples of control-release materials include enteric polymers, hydroxypropyl methylcellulose.

The amount of the various classes of constituents that comprise the carrier can be selected by the user to achieve the desired effects.

The examples below are illustrative of the present invention and compare the present invention to prior art compositions.

EXAMPLES

Antisense oligonucleotides were synthesized by solid phase organic synthesis using appropriately protected synthons. Reversed phase chromatography is used to purify the antisense oligonucleotide, which is then deprotected and lyophilized.

Example 1

Compositions Including an Antisense Oligonucleotide Targeting Human TNF-α

An example of a formulation containing an enhancer of the present development and an antisense oligonucleotide is a composition comprising sodium 2-n-octyl-dodecanoate, sodium caprate and an antisense oligonucleotide, which targets TNFα. This antisense oligonucleotide is a 2'-O-(2-methoxyethyl) modified phosphorothioate oligonucleotide containing a 10-base 2' deoxy gap, also referred to as a 5-10-5 MOE gapmer, with 2' MOE modification of only the five nucleotides at the 3' and 5' termini of the oligonucleotide wherein each of the 19 inter-nucleotide linkages is an O,O-linked phosphorothioate. In addition, all cytosines are modified to 5-methylcytosines. The 2' MOE modification makes an oligonucleotide more resistant to nuclease degradation, thereby improving both its RNA binding affinity and increasing its half life. This antisense oligonucleotide targets human TNF-α and can be used to treat inflammatory disorders, such as rheumatoid arthritis. The antisense oligonucleotide has a sequence of:

GCT GAT TAG AGA GAG GTC CC    (SEQ ID NO.: 1)

Example 2

Compositions Including an Antisense Oligonucleotide Targeting c-raf Kinase

An antisense oligonucleotide treatment composition will be prepared comprising sodium 2-n-octyl-dodecanoate, sodium caprate, and an antisense oligonucleotide which targets human c-raf kinase which can be used to treat hyperproliferation disorders, such as various forms of cancer. The antisense oligonucleotide has a sequence of:

TCC CGC CTG TGA CAT GCA TT    (SEQ ID NO.: 2)

Each of the inter-nucleotide linkages is an O,O-linked phosphorothioate.

Example 3

Compositions Including an Antisense Oligonucleotide Targeting Human Papillomavirus An antisense oligonucleotide treatment composition will be prepared comprising sodium 2-n-octyl-dodecanoate, sodium caprate, and an antisense oligonucleotide which targets human papillomavirus which can be used to treat warts including, for example, genital warts. The antisense oligonucleotide has a sequence of:

TTG CTT CCA TCT TCC TCG TC    (SEQ ID NO.: 3)

Each of the inter-nucleotide linkages is an O,O-linked phosphorothioate.

Example 4

Compositions Including an Antisense Oligonucleotide Targeting Intercellular Adhesion Molecule-1(ICAM-1)

An antisense oligonucleotide treatment composition will be prepared comprising sodium 2-n-octyl-dodecanoate, sodium caprate and an antisense oligonucleotide which targets the intercellular adhesion molecule-1(ICAM-1) and can be used to treat inflammatory disorders, for example, inflammatory bowel disorders, psoriasis and rheumatoid arthritis. The antisense oligonucleotide has a sequence of:

CCC CAC CAC TTC CCC TCT C    (SEQ ID NO.: 4)

Each of the inter-nucleotide linkages is an O,O-linked phosphorothioate.

Example 5

Composition Including Sodium 2-n-octyl-dodecanoate

Compositions comprising sodium caprate and an antisense compound with and without an enhancer compound of the present development, sodium 2-n-octyl-dodecanoate, were administered to animals to demonstrate the enhanced bioavailability of macromolecular compounds for example, oligo- and polynucleotides, afforded by the enhancer compounds of the present development. The ratio of enhancer and antisense compounds in the compositions is shown in Table 6.

Antisense oligonucleotides were synthesized by solid phase organic synthesis using appropriately protected synthons. Reversed phase chromatography was used to purify the antisense oligonucleotide, which was then deprotected and lyophilized.

The antisense oligonucleotide used was a 2'-O-(2-methoxyethyl) modified phosphorothioate oligonucleotide containing a 10-base 2' deoxy gap, also referred to as a 5-10-5 MOE gapmer, with 2' MOE modification of only the five nucleotides at the 3' and 5' termini of the oligonucleotide wherein each of the 19 inter-nucleotide linkages is an O,O-linked phosphorothioate. In addition, all cytosines are modified to be 5-methylcytosines. The 2' MOE modification makes an oligonucleotide more resistant to nuclease degradation, thereby improving both its RNA binding affinity and increasing its half life. This antisense oligonucleotide targets human TNF-α to treat inflammatory disorders, such as rheumatoid arthritis. This antisense oligonculeotide has a sequence of:

GCT GAT TAG AGA GAG GTC CC    (SEQ ID NO.: 1)

The compositions were compared by administering them in solution form through a catheter to test subjects. A jejunal catheter is surgically implanted in six male rhesus monkeys (3-5 years, 3-5 Kg) under anesthesia. The catheters are attached to a subcutaneous access port to allow dosing through the port into the jejunum. The animals are allowed to recover at least 7 days prior to dosing. Animals were fasted overnight prior to dosing and fed 2 hours post-dosing. Test formulations are prepared in water and are dosed to animals as a bolus (0.5 ml/kg) in a cross-over study design with a one week wash out period between each dose. Whole blood samples are taken from the femoral vein (other than the dosing site for intravenous administration) at the following time intervals: 0 (pre-dose) 2, 5, 10, 20, 30, 45, 60, 90, 120, 180, 240 and 360 minutes for intravenous dose and at 0 (pre-dose), 5, 15, 30, 45, 60, 90, 120, 150, 180, 240, 360 and 480 minutes for intrajejunal doses. The samples are collected in EDTA-containing tubes and centrifuged in a refrigerated centrifuge (2-8° C.) to obtain plasma that is stored at -70° C. until analysis. The antisense oligonucleotide is detected by anion-exchange chromatography.

The formulations and the measurements bioavailability, Tmax and plasma peak of antisense oligonucleotide after administration of formulations are described in the chart below. The bioavailability (i.e. relative to an intravenous dose) is calculated from the areas under the curve obtained from plasma oligonucleotide concentration-time profiles.

TABLE 6

| PK parameters | Antisense Oligonucleotide (10 mg/kg) Sodium caprate (50 mg/kg) | Antisense Oligonucleotide (10 mg/kg) Sodium 2-n-octyl-dodecanoate (15 mg/kg) + Sodium caprate (35 mg/kg) |
|---|---|---|
| Peak plasma (g/ml) | 2.7 ± 1.5 | 8.7 ± 3.8* |
| Tmax (min) | 19 ± 12 | 30 ± 9 |
| AUC (g · min/ml) | 127 ± 8.7 | 451 ± 224* |
| % Bioavailability | 3.0 ± 2.1 | 10.8 ± 5.4* |

Results of above table are expressed as mean ± SD (n = 6), AUC = area under concentration-time curve, $T_{max}$ = time to reach peak plasma concentration;
*p < 0.05.

The antisense oligonucleotide has poor permeability when administered to monkeys orally or intra-intestinally without any permeation enhancer systems. This bioavailability is significantly improved when the drug is dosed with a permeation enhancer. The highest bioavailability is observed with compositions including the permeation enhancer sodium 2-n-octyl-dodecanoate, in which bioavailability ranged from 5.2% to 18.2%. The enhancement of bioavailability with the branched chain enhancer compound relative to the straight chain sodium caprate alone is not only related to the increase in plasma peak but also to a significant increase in the overall area under the curve. The bioavailability achieved with compositions containing only the straight chain carboxylic acid salt, sodium caprate, ranged from 1.0% to 6.2%, a significantly reduced permeation enhancing effect.

We claim:

1. A pharmaceutical composition comprising:
   (a) an antisense compound;
   (b) a branched chain permeation enhancer comprising an acid functional group-containing compound of Formula I in which at least about 50% of the total number of acid functional groups present have been reacted with a base, the compound of Formula I comprising:

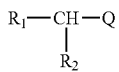

wherein:
   Q is selected from the group consisting of a —COOH functional group, a —SO$_3$H functional group, an alkyl or alkenyl group having one to about 12 carbon atoms which is mono- or di-substituted with a substituent selected independently for each occurrence from the group consisting of a —COOH functional group and a —SO$_3$H functional group;
   R$_1$ and R$_2$ are selected independently from the group consisting of an alky or alkenyl group from one to about 12 carbon atoms which is optionally substituted with a functional group selected independently for each occurrence from the group consisting of a —COOH functional group, a —SO$_3$H functional group, an —NH$_2$ functional group, a —CONH$_2$ functional group, and a —OH functional group; and (c) a pharmaceutically acceptable vehicle,
   wherein said antisense compound and permeation enhancer are combined in a composition formulated for transdermal administration or transmucosal administration, and wherein the permeation enhancer is present in an amount sufficient to increase the bioavailability of the antisense compound upon transdermal administration or transmucosal administration of the composition to a patient.

2. The composition of claim 1 wherein R$_1$ and R$_2$ are independently an unsubstituted linear alkyl group having from one to about 12 carbon atoms.

3. The composition of claim 2 wherein said enhancer is selected from the group consisting of sodium 2-n-octyl-dodecanoate, sodium 2-n-hexyl-decanoate, and sodium 2-n-butyl-octanoate.

4. The composition of claim 3 wherein the antisense compound is an antisense oligonucleotide.

5. The composition of claim 3 further comprising a linear fatty acid salt.

6. The composition of claim 5 wherein said linear fatty acid salt is sodium caprate.

7. The composition of claim 6 having a ratio of said sodium 2-n-octyl-dodecanoate : said sodium caprate up to about 3:7.

8. The composition of claim 4 wherein the antisense oligonucleotide comprises a modification selected from the group consisting of base modifications, internucleotide linkage modifications and sugar moiety modifications.

9. The composition of claim 8 wherein said sugar moiety modification is a 2'-O-(2-methoxyethyl) modification.

10. The composition of claim 1, wherein said composition is in oral dosage form.

11. A method of providing for enhanced uptake of an antisense oligonucleotide compound in a patient comprising transdermally administering or transmucosally administering to said patient the composition of claim 1.

12. The method of claim 11, wherein said composition is administered orally.

13. The method of claim 11 wherein $R_1$ and $R_2$ are independently an unsubstituted linear alkyl group having from one to about 12 carbon atoms.

14. The method of claim 11 wherein said enhancer is selected from the group consisting of sodium 2-n-octyl-dodecanoate, sodium 2-n-hexyl-decanoate, and sodium 2-n-butyl-octanoate.

15. The method of claim 14 wherein the antisense compound is an antisense oligonucleotide.

16. The method of claim 14 further comprising a linear fatty acid salt.

17. The method of claim 16 wherein said linear fatty acid salt is sodium caprate.

18. The method of claim 17 having a ratio of said sodium 2-n-octyl-dodecanoate : said sodium caprate up to about 3:7.

19. The method of claim 11, wherein said antisense compound is a 20 nucleobase long modified oligonucleotide comprising:

a gap segment consisting of ten linked deoxynucleosides;
a 5' wing segment consisting of five linked nucleosides;
a 3' wing segment consisting of five linked nucleosides;
wherein the gap segment is positioned between the 5' wing segment and the 3' wing segment, wherein each nucleoside of each wing segment comprises a 2'-O-methoxyethyl sugar, wherein each internucleoside linkage of said modified oligonucleotide is a phosphorothioate linkage, and wherein each cytosine of said modified oligonucleotide is a 5-methylcytosine;
wherein said branched chain permeation enhancer is sodium 2-n-octyl-dodecanoate;
wherein said composition further comprises sodium caprate in a ratio of sodium 2-n-octyl-dodecanoate to sodium caprate of about 3:7; and
wherein said composition is administered orally.

20. The composition of claim 1 wherein $R_1$ is an unsubstituted linear alkyl group having from 4 to 8 carbon atoms, $R_2$ is an unsubstituted linear alkyl group having from 8 to 12 carbon atoms, and Q is a —COOH functional group.

* * * * *

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Antisense oligonucleotide
<220> FEATURE:
<221> NAME/KEY: modified_base
<222> LOCATION: (1)...(20)
<223> OTHER INFORMATION: Phosphorothioate oligonucleotide
<220> FEATURE:
<221> NAME/KEY: modified_base
<222> LOCATION: (2)...(2)
<223> OTHER INFORMATION: m5c
<220> FEATURE:
<221> NAME/KEY: modified_base
<222> LOCATION: (18)...(20)
<223> OTHER INFORMATION: m5c
<220> FEATURE:
<221> NAME/KEY: modified_base
<222> LOCATION: (1)...(5)
<223> OTHER INFORMATION: 2'-O-(2-methoxyethyl) modified
<220> FEATURE:
<221> NAME/KEY: modified_base
<222> LOCATION: (6)...(20)
<223> OTHER INFORMATION: 2'-O-(2-methoxyethyl) modified

<400> SEQUENCE: 1
gctgattaga gagaggtccc                                                    20

<210> SEQ ID NO 2
<211> LENGTH: 20
<212> TYPE: DNA
<213> ORGANISM: Artificial Sequence
<220> FEATURE:
<223> OTHER INFORMATION: Antisense oligonucleotide
<220> FEATURE:
<221> NAME/KEY: modified_base
```

```
<222> LOCATION: (1)...(20)
<223> OTHER INFORMATION: Phosphorothioate oligonucleotide

<400> SEQUENCE: 2
tcccgcctgt gacatgcatt                                              20

<210> SEQ ID NO 3
<211> LENGTH: 20
<212> TYPE: DNA
<213> ORGANISM: Artificial Sequence
<220> FEATURE:
<223> OTHER INFORMATION: Antisense oligonucleotide
<220> FEATURE:
<221> NAME/KEY: modified_base
<222> LOCATION: (1)...(20)
<223> OTHER INFORMATION: Phosphorothioate oligonucleotide

<400> SEQUENCE: 3
ttgcttccat cttcctcgtc                                              20

<210> SEQ ID NO 4
<211> LENGTH: 19
<212> TYPE: DNA
<213> ORGANISM: Artificial Sequence
<220> FEATURE:
<223> OTHER INFORMATION: Antisense oligonucleotide
<220> FEATURE:
<221> NAME/KEY: modified_base
<222> LOCATION: (1)...(20)
<223> OTHER INFORMATION: Phosphorothioate oligonucleotide

<400> SEQUENCE: 4
ccccaccact tccctctc                                                19
```